US012660066B2

(12) United States Patent
Lucassen et al.

(10) Patent No.: US 12,660,066 B2
(45) Date of Patent: Jun. 16, 2026

(54) MELANOPIC LIGHT SENSITIVITY

(71) Applicant: SIGNIFY HOLDING B.V., Eindhoven (NL)

(72) Inventors: Marcel Petrus Lucassen, Landsmeer (NL); Remy Cyrille Broersma, Eindhoven (NL); Tobias Borra, Rijswijk (NL); Bianca Maria Irma Van Der Zande, Heeze (NL)

(73) Assignee: SIGNIFY HOLDING B.V., Eindhoven (NL)

( * ) Notice: Subject to any disclaimer, the term of this patent is extended or adjusted under 35 U.S.C. 154(b) by 57 days.

(21) Appl. No.: 18/859,686

(22) PCT Filed: Apr. 18, 2023

(86) PCT No.: PCT/EP2023/059970
§ 371 (c)(1),
(2) Date: Oct. 24, 2024

(87) PCT Pub. No.: WO2023/208642
PCT Pub. Date: Nov. 2, 2023

(65) Prior Publication Data
US 2025/0294659 A1 Sep. 18, 2025

(30) Foreign Application Priority Data
Apr. 25, 2022 (EP) ..................................... 22169699

(51) Int. Cl.
*H05B 47/16* (2020.01)
*A61M 21/02* (2006.01)
(Continued)

(52) U.S. Cl.
CPC ............. *H05B 47/16* (2020.01); *A61M 21/02* (2013.01); *H05B 45/10* (2020.01); *H05B 45/20* (2020.01);
(Continued)

(58) Field of Classification Search
CPC ........ H05B 47/16; H05B 45/10; H05B 45/20; H05B 47/115; H05B 47/196; H05B 47/19;
(Continued)

(56) References Cited

U.S. PATENT DOCUMENTS 10,349,484 B1 * 7/2019 Zhang .................... H05B 45/20
11,071,187 B1 7/2021 Maa et al.
(Continued)

FOREIGN PATENT DOCUMENTS

WO WO-2021194429 A1 * 9/2021 ............. H05B 45/20
WO WO-2021199752 A1 * 10/2021 ......... H10H 20/8513
(Continued)

*Primary Examiner* — Adam D Houston

(57) ABSTRACT

The invention provides a light generating system (1000) comprising one or more light generating devices (100), wherein each of the one or more light generating devices (100) are configured to generate device light (101), wherein the light generating system (1000) is configured to generate system light (1001) comprising the device light (101) of at least one light generating device (100), wherein the light generating system (1000) is configured to provide (in an operational mode) system light (1001) according to the following characteristics: (A) during a first time period t1 the system light (1001) is white light having a radiant flux $\Phi 11$ in a first wavelength range and a radiant flux $\Phi 12$ in a second wavelength range; (B) during a second time period t2 the system light (1001) is light having a radiant flux $\Phi 21$ in the first wavelength range and a radiant flux $\Phi 22$ in the second wavelength range; (C) during a third time period t3 the system light (1001) is light having a radiant flux $\Phi 31$ in the first wavelength range and a radiant flux $\Phi 32$ in the second wavelength range; (D) $\Phi 21 < \Phi 11$ and $\Phi 31 < \Phi 11$; (E) $\Phi 22 > \Phi 12$, and $\Phi 32 < \Phi 12$; (F) t2 is selected from the range of 1 second-30 minutes; and t1>t2; and (G) the first wave- (Continued)

length range is 380 nm-λ1 and the second wavelength range is λ1-780 nm, wherein λ1 is selected from the range of 485-550 nm.

12 Claims, 5 Drawing Sheets

(51) Int. Cl.

| | |
|---|---|
| *H05B 45/10* | (2020.01) |
| *H05B 45/20* | (2020.01) |
| *H05B 47/115* | (2020.01) |
| *H05B 47/175* | (2020.01) |
| *A61M 21/00* | (2006.01) |
| *H05B 47/19* | (2020.01) |

(52) U.S. Cl.
CPC ......... *H05B 47/115* (2020.01); *H05B 47/196* (2024.01); *A61M 2021/0044* (2013.01); *H05B 47/19* (2020.01)

(58) Field of Classification Search
CPC .......... A61M 21/02; A61M 2021/0044; A61M 2205/3546; A61M 2230/005
See application file for complete search history.

(56) References Cited

U.S. PATENT DOCUMENTS

| | | | | |
|---|---|---|---|---|
| 11,209,138 | B2 * | 12/2021 | Keller | .................... F21V 23/003 |
| 2010/0244735 | A1 * | 9/2010 | Buelow, II | ............. H05B 35/00 |
| | | | | 315/320 |
| 2012/0008326 | A1 * | 1/2012 | Jou | ......................... A61M 21/02 |
| | | | | 362/293 |
| 2013/0119891 | A1 | 5/2013 | Herremans et al. | |
| 2017/0208673 | A1 | 7/2017 | Schlangen et al. | |
| 2017/0348506 | A1 * | 12/2017 | Berman | ................. H05B 47/16 |
| 2018/0235041 | A1 | 8/2018 | Trouwborst et al. | |
| 2019/0353328 | A1 * | 11/2019 | Pickard | .................. H05B 45/20 |
| 2019/0387593 | A1 | 12/2019 | Paulsen et al. | |
| 2021/0031050 | A1 * | 2/2021 | Do | ......................... H05B 45/10 |
| 2021/0215317 | A1 * | 7/2021 | Pickard | ................ G02B 6/0031 |
| 2024/0003518 | A1 * | 1/2024 | Pickard | .................... F21V 13/02 |
| 2025/0020310 | A1 * | 1/2025 | Harrison | ............. G02B 6/0045 |
| 2025/0294659 | A1 * | 9/2025 | Lucassen | ............... H05B 47/16 |

FOREIGN PATENT DOCUMENTS

| | | | | |
|---|---|---|---|---|
| WO | WO-2023006471 A1 * | 2/2023 | ............. H05B 47/17 |
| WO | WO-2023110510 A1 * | 6/2023 | ............... A61L 9/20 |
| WO | WO-2023208642 A1 * | 11/2023 | ............ A61M 21/02 |
| WO | WO-2024028137 A1 * | 2/2024 | ............... F21V 9/30 |
| WO | WO-2025172149 A1 * | 8/2025 | ............ H10H 29/24 |

* cited by examiner $$y = -0.8265x + 1.8207$$
$$R^2 = 0.9991$$

MELANOPIC LIGHT SENSITIVITY

CROSS-REFERENCE TO PRIOR APPLICATIONS

This application is the U.S. National Phase application under 35 U.S.C. § 371 of International Application No. PCT/EP2023/059970, filed on Apr. 18, 2023, which claims the benefit of European Patent Application No. 22169699.0, filed on Apr. 25, 2022. These applications are hereby incorporated by reference herein.

FIELD OF THE INVENTION

The invention relates to a light generating system and to a lighting device comprising such light generating system.

BACKGROUND OF THE INVENTION

Lighting devices designed for a circadian effect are known in the art. For instance, U.S. Ser. No. 11/071,187 describes a circadian entrainment enhancement device including a housing, a first directional light source, a second directional light source, and a driver. During daytime, the driver turns on the first directional light source with a high melanopic ratio to enhance the daytime circadian entrainment of a user. During nighttime, the driver turns on the second directional light source with a low melanopic ratio to enhance the nighttime circadian entrainment of a user. U.S. Ser. No. 11/071,187 also describes using a light sensor, a memory module, and a computation module to calculate the necessary light output of the device by factoring the ambient light level into consideration. U.S. Ser. No. 11/071,187 also describes using a distance sensor to adjust the light level of the light sources according to the distance between the device and the user.

US 2013/0119891 A1 discloses a method for controlled lighting of an area with a lighting system, wherein the method comprises providing with the lighting system, according to a predetermined time program, general lighting during a predetermined general lighting period and colored lighting during a predetermined first colored lighting period. The predetermined time program runs for at least 6 hours. Further, in the method a control unit is applied, configured to control the lighting system according to the predetermined time program.

US 2019/0387593 A1 discloses an exemplary device configured to emit a first light having a first luminous flux and a peak intensity at a first wavelength that is greater than or equal to 400 nanometers (nm) and less than or equal to 480 nm. The first luminous flux is variable and/or the emission of the first light is interrupted one or more times. The device is also configured to emit a second light having a second luminous flux and a peak intensity at a second wavelength that is greater than or equal to 500 nm and less than or equal to 630 nm. The second luminous flux is variable and/or the emission of the second light is interrupted one or more times. The first luminous flux is at a maximum at least during a time at which the second luminous flux is not at a maximum.

SUMMARY OF THE INVENTION

It seems that bright light in the evening, and in particular short wavelength light, may be able to suppress the natural build-up of melatonin, the pineal hormone involved in preparing our body for sleep. The mechanism underlying the suppression of melatonin may start with the absorption of light in the melanopsin photopigment, present in a small percentage of retinal ganglion cells (ipRGCs). These cells may be able to signal to the brain (SCN), causing a change in the signal to start synthesis of melatonin in the pineal gland. Hence, the melatonin production seems negatively affected by the stimulation of melanopsin by light. The strength of melanopsin stimulation is quantified by the melanopic EDI (herein abbreviated as MEDI), see e.g. also: 2018 CIE S 026—CIE system for metrology of optical radiation for ipRGC-influenced responses to light (which is herein incorporated by reference). The extent to which light may stimulate melanopsin, and thereby the potential to affect (the suppression of) melatonin production, may be quantified by the melanopic equivalent daylight illuminance, also known as melanopic EDI or MEDI. It seems that the lower the MEDI in the evening, the better the preparation for sleep. Lighting applications that support the going-to-bed routine may therefore aim for a low MEDI during the evening; preferably a MEDI of 10 1×2-3 hours before bedtime. One strategy is to reduce the illuminance level. Another strategy is to shift to low CCT values (e.g., 2700 K or even 2200 K) and/or to modify the light spectrum to minimize the radiance in the cyan part of the spectrum where melanopsin is most sensitive. However, there is a desire to provide improved lighting devices which may have a different or better impact on the circadian rhythm.

Hence, it is an aspect of the invention to provide an alternative light generating system, which preferably further at least partly obviates one or more of above-described drawbacks. The present invention may have as object to overcome or ameliorate at least one of the disadvantages of the prior art, or to provide a useful alternative.

According to a first aspect, the invention provides a light generating system ("system") comprising one or more light generating devices, wherein each of the one or more light generating devices are configured to generate device light. In embodiments, the light generating system may be configured to generate system light comprising the device light of at least one light generating device (of the one or more light generating devices). Especially, in embodiments the light generating system may be configured to provide (in an operational mode) system light according to the following characteristics: (a) during a first time period t1 the system light is visible light, more especially white light, and (b) during a second time period t2 the system light has a different spectral power distribution than the system light during the first time period. Optionally, during a third time period t3 system light may be provided having a spectral power distribution which may be the same as during the first period, or during the second period, or may be different from both. In specific embodiments, during a first time period t1 the system light may be (white) light having a radiant flux $\Phi 11$ in a first wavelength range and a radiant flux $\Phi 12$ in a second wavelength range; during a second time period t2 the system light may be light having a radiant flux $\Phi 21$ in the first wavelength range and a radiant flux $\Phi 22$ in the second wavelength range; and optionally during a third time period t3 the system light may be light having a radiant flux $\Phi 31$ in the first wavelength range and a radiant flux $\Phi 32$ in the second wavelength range. Especially, in embodiments the following conditions may apply: $\Phi 21 < \Phi 11$, $\Phi 22 > \Phi 12$, t2 is selected from the range of 1 second-30 minutes, and the first wavelength range may be 380 nm-$\lambda 1$ and the second wavelength range may be $\lambda 1$-780 nm, wherein $\lambda 1$ may be selected from the range of 485-550 nm. Further, in embodiments (also) the following conditions may apply: $\Phi 31 < \Phi 11$, $\Phi32<\Phi12$, and $t1>t2$. Therefore, especially the invention provides a light generating system comprising one or more light generating devices, wherein each of the one or more light generating devices are configured to generate device light, wherein the light generating system is configured to generate system light comprising the device light of at least one light generating device, wherein the light generating system is configured to provide (in an operational mode) system light according to the following characteristics: (A) during a first time period t1 the system light is visible light, especially white light, having a radiant flux $\Phi11$ in a first wavelength range and a radiant flux $\Phi12$ in a second wavelength range; (B) during a second time period t2 the system light is light having a radiant flux $\Phi21$ in the first wavelength range and a radiant flux $\Phi22$ in the second wavelength range; (C) during a third time period t3 the system light is light having a radiant flux $\Phi31$ in the first wavelength range and a radiant flux $\Phi32$ in the second wavelength range; (D) $\Phi21<\Phi11$ and $\Phi31<\Phi11$; (E) $\Phi22>\Phi12$, and $\Phi32<\Phi12$; (F) t2 is selected from the range of 1 second-30 minutes; and t1>t2; and (G) the first wavelength range is 380 nm-$\lambda1$ and the second wavelength range is $\lambda1$-780 nm, wherein $\lambda1$ is selected from the range of 485-550 nm.

With such system, a kind of booster light pulse may be provided which may unexpectedly have an advantageous effect on the circadian rhythm. Instead of reducing the intensity, a relatively intense pulse of light may be provided shortly before sleeping, which may have an advantageous effect. Without being bound to theory, the invention may use the (counter-intuitive) application of a brief and relatively high-intensity light to force part of the melanopsin pigment (the part that can actively contribute to brain signaling) in a silent state. This may effectively reduce the disturbance of melatonin build-up by light and as such is beneficial in the preparation for going to sleep. Hence, the invention may provide amongst others a go-to-sleep routine, including a booster light pulse.

As indicated above, the light generating system may comprise one or more light generating devices. Especially, each of the one or more light generating devices may be configured to generate device light. A light generating device may especially be configured to generate device light. Especially, the light generating device may comprise a light source. The light source may especially be configured to generate light source light. In embodiments, the device light may essentially consist of the device light. In other embodiments, the device light may essentially consist of converted light source light. In yet other embodiments, the device light may comprise (unconverted) light source light and converted light source light. Light source light may be converted with a luminescent material into luminescent material light and/or with an upconverter into upconverted light (see also below). The term "light generating device" may also refer to a plurality of light generating devices which may provide device light having essentially the same spectral power distributions. In specific embodiments, the term "light generating device" may also refer to a plurality of light generating devices which may provide device light having different spectral power distributions.

The term "light source" may in principle relate to any light source known in the art. It may be a conventional (tungsten) light bulb, a low pressure mercury lamp, a high pressure mercury lamp, a fluorescent lamp, an LED (light emissive diode). In a specific embodiment, the light source comprises a solid state LED light source (such as an LED or laser diode (or "diode laser")). The term "light source" may also relate to a plurality of light sources, such as 2-2000 (solid state) LED light sources. Hence, the term LED may also refer to a plurality of LEDs. Further, the term "light source" may in embodiments also refer to a so-called chips-on-board (COB) light source. The term "COB" especially refers to LED chips in the form of a semiconductor chip that is neither encased nor connected but directly mounted onto a substrate, such as a PCB. Hence, a plurality of light emitting semiconductor light source may be configured on the same substrate. In embodiments, a COB is a multi LED chip configured together as a single lighting module.

The light source may have a light escape surface. Referring to conventional light sources such as light bulbs or fluorescent lamps, it may be an outer surface of a glass or a quartz envelope. For LED's it may for instance be the LED die, or when a resin is applied to the LED die, the outer surface of the resin. In principle, it may also be the terminal end of a fiber. The term escape surface especially relates to that part of the light source, where the light actually leaves or escapes from the light source. The light source is configured to provide a beam of light. This beam of light (thus) escapes from the light exit surface of the light source.

Likewise, a light generating device may comprise a light escape surface, such as an end window. Further, likewise a light generating system may comprise a light escape surface, such as an end window.

The term "light source" may refer to a semiconductor light-emitting device, such as a light emitting diode (LEDs), a resonant cavity light emitting diode (RCLED), a vertical cavity laser diode (VCSELs), an edge emitting laser, etc. . . . The term "light source" may also refer to an organic light-emitting diode (OLED), such as a passive-matrix (PMOLED) or an active-matrix (AMOLED). In a specific embodiment, the light source comprises a solid-state light source (such as an LED or laser diode). In an embodiment, the light source comprises an LED (light emitting diode). The terms "light source" or "solid state light source" may also refer to a superluminescent diode (SLED).

The term LED may also refer to a plurality of LEDs.

The term "light source" may also relate to a plurality of (essentially identical (or different)) light sources, such as 2-2000 solid state light sources. In embodiments, the light source may comprise one or more micro-optical elements (array of micro lenses) downstream of a single solid-state light source, such as an LED, or downstream of a plurality of solid-state light sources (i.e. e.g. shared by multiple LEDs). In embodiments, the light source may comprise an LED with on-chip optics. In embodiments, the light source comprises pixelated single LEDs (with or without optics) (offering in embodiments on-chip beam steering).

In embodiments, the light source may be configured to provide primary radiation, which is used as such, such as e.g. a blue light source, like a blue LED, or a green light source, such as a green LED, and a red light source, such as a red LED. Such LEDs, which may not comprise a luminescent material ("phosphor") may be indicated as direct color LEDs.

In other embodiments, however, the light source may be configured to provide primary radiation and part of the primary radiation is converted into secondary radiation. Secondary radiation may be based on conversion by a luminescent material. The secondary radiation may therefore also be indicated as luminescent material radiation. The luminescent material may in embodiments be comprised by the light source, such as an LED with a luminescent material layer or dome comprising luminescent material. Such LEDs may be indicated as phosphor converted LEDs or PC LEDs (phosphor converted LEDs). In other embodiments, the luminescent material may be configured at some distance ("remote") from the light source, such as an LED with a luminescent material layer not in physical contact with a die of the LED. Hence, in specific embodiments the light source may be a light source that during operation emits at least light at wavelength selected from the range of 380-470 nm. However, other wavelengths may also be possible. This light may partially be used by the luminescent material.

In embodiments, the light generating device may comprise a luminescent material. In embodiments, the light generating device may comprise a PC LED. In other embodiments, the light generating device may comprise a direct LED (i.e. no phosphor). In embodiments, the light generating device may comprise a laser device, like a laser diode. In embodiments, the light generating device may comprise a superluminescent diode. Hence, in specific embodiments, the light source may be selected from the group of laser diodes and superluminescent diodes. In other embodiments, the light source may comprise an LED.

The light source may especially be configured to generate light source light having an optical axis (O), (a beam shape,) and a spectral power distribution. The light source light may in embodiments comprise one or more bands, having band widths as known for lasers.

The term "light source" may (thus) refer to a light generating element as such, like e.g. a solid state light source, or e.g. to a package of the light generating element, such as a solid state light source, and one or more of a luminescent material comprising element and (other) optics, like a lens, a collimator. A light converter element ("converter element" or "converter") may comprise a luminescent material comprising element. For instance, a solid state light source as such, like a blue LED, is a light source. A combination of a solid state light source (as light generating element) and a light converter element, such as a blue LED and a light converter element, optically coupled to the solid state light source, may also be a light source (but may also be indicated as light generating device). Hence, a white LED is a light source (but may e.g. also be indicated as (white) light generating device).

The term "light source" herein may also refer to a light source comprising a solid state light source, such as an LED or a laser diode or a superluminescent diode.

The term "light source" may (thus) in embodiments also refer to a light source that is (also) based on conversion of light, such as a light source in combination with a luminescent converter material. Hence, the term "light source" may also refer to a combination of an LED with a luminescent material configured to convert at least part of the LED radiation, or to a combination of a (diode) laser with a luminescent material configured to convert at least part of the (diode) laser radiation.

In embodiments, the term "light source" may also refer to a combination of a light source, like an LED, and an optical filter, which may change the spectral power distribution of the light generated by the light source. Especially, the term "light generating device" may be used to address a light source and further (optical components), like an optical filter and/or a beam shaping element, etc.

The phrases "different light sources" or "a plurality of different light sources", and similar phrases, may in embodiments refer to a plurality of solid-state light sources selected from at least two different bins. Likewise, the phrases "identical light sources" or "a plurality of same light sources", and similar phrases, may in embodiments refer to a plurality of solid-state light sources selected from the same bin.

The term "solid state light source", or "solid state material light source", and similar terms, may especially refer to semiconductor light sources, such as a light emitting diode (LED), a diode laser, or a superluminescent diode.

Especially, the light generating system is configured to generate system light. The system light may comprise the device light of at least one light generating device (of the one or more light generating devices). More especially, the system light may essentially consist of the device light of at least one light generating device. Especially, the system light has a controllable spectral power distribution and a controllable radiant flux. The term "radiant flux" may especially refer to the radiant energy emitted per unit time (by the light generating device). Instead of the term "radiant flux", also the terms "intensity" or "radiant power" may be applied. The term "radiant flux" may have as unit an energy, like especially Watts. The term "spectral power distribution" may especially refer to the power distribution of the light (especially in Watts) as function of the wavelength (especially in nanometers), especially in embodiments over the human visible wavelength range (380-780 nm). Especially, the term "spectral power distribution" may refer to a radiant flux per unit frequency or wavelength, often indicated in Watt/nm. Instead of the term "spectral power distribution" also the term "spectral flux" may be applied. Hence, instead of the phrase "controllable spectral power distribution", also the phrase "controllable spectral flux" may be applied. The spectral flux may be indicated as power (Watt) per unit frequency or wavelength. Especially, herein the spectral flux is indicated as the radiant flux per unit wavelength (W/nm). Further, herein spectral fluxes and radiant fluxes are especially based on the spectral power of the device light over the 380-780 nm wavelength range. The term "correlated color temperature" may herein especially refer to the temperature of a Planckian radiator having the chromaticity nearest the chromaticity associated with the given spectral distribution on a modified 1976 UCS diagram where u', 2/3v' are the coordinates of the Planckian locus and the test stimulus.

As the system light may be controllable, especially the spectral power distribution and the radiant flux may be controlled. To this end, especially the system may comprise a light generating device having a controllable spectral power distribution and/or comprise two or more light generating devices. In the former embodiment(s), the light generating device having a controllable spectral power distribution may be controlled by a control system. In the latter embodiment(s) the spectral power distribution of the system light may be controlled by controlling the two or more light generating devices by a control system.

Therefore, especially the light generating system may comprise a control system or may be functionally coupled to a control system. The control system may especially be configured to control the one or more light generating devices. In embodiments wherein there are more than one light generating device, the control system may be configured to control the light generating devices individually (or control sets of light generating devices individually (see also below)). Especially, the control system may be configured to control the system light (more especially the radiant flux and spectral power distribution of the system light).

The term "controlling", and similar terms, herein may especially refer at least to determining the behavior or supervising the running of an element. Hence, herein "controlling" and similar terms may e.g. refer to imposing behavior to the element (determining the behavior or supervising the running of an element), etc., such as e.g. measuring, displaying, actuating, opening, shifting, changing temperature, etc. Beyond that, the term "controlling" and similar terms may additionally include monitoring. Hence, the term "controlling" and similar terms may include imposing behavior on an element and also imposing behavior on an element and monitoring the element. The controlling of the element can be done with a control system, which may also be indicated as "controller". The control system and the element may thus at least temporarily, or permanently, functionally be coupled. The element may comprise the control system. In embodiments, the control system and element may not be physically coupled. Control can be done via wired and/or wireless control. The term "control system" may also refer to a plurality of different control systems, which especially are functionally coupled, and of which e.g. one control system may be a master control system and one or more others may be slave control systems. A control system may comprise or may be functionally coupled to a user interface.

The control system may also be configured to receive and execute instructions from a remote control. In embodiments, the control system may be controlled via an App on a device, such as a portable device, like a Smartphone or I-phone, a tablet, etc. The device is thus not necessarily coupled to the light generating system, but may be (temporarily) functionally coupled to the light generating system.

Hence, in embodiments the control system may (also) be configured to be controlled by an App on a remote device. In such embodiments the control system of the light generating system may be a slave control system or control in a slave mode. For instance, the light generating system may be identifiable with a code, especially a unique code for the respective light generating system. The control system of the light generating system may be configured to be controlled by an external control system which has access to the light generating system on the basis of knowledge (input by a user interface or with an optical sensor, e.g., QR code reader) of the (unique) code. The light generating system may also comprise means for communicating with other systems or devices, such as on the basis of Bluetooth, WiFi, LiFi, ZigBee, BLE or WiMAX, or another wireless technology.

The system, or apparatus, or device may execute an action in a "mode" or "operation mode" or "mode of operation" or "operational mode". The term "operational mode may also be indicated as "controlling mode". Likewise, in a method an action or stage, or step may be executed in a "mode" or "operation mode" or "mode of operation" or "operational mode". This does not exclude that the system, or apparatus, or device may also be adapted for providing another controlling mode, or a plurality of other controlling modes. Likewise, this may not exclude that before executing the mode and/or after executing the mode one or more other modes may be executed.

However, in embodiments a control system may be available, that is adapted to provide at least the controlling mode. Would other modes be available, the choice of such modes may especially be executed via a user interface, though other options, like executing a mode in dependence of a sensor signal or a (time) scheme, may also be possible. The operation mode may in embodiments also refer to a system, or apparatus, or device, that can only operate in a single operation mode (i.e. "on", without further tunability).

Hence, in embodiments, the control system may control in dependence of one or more of an input signal of a user interface, a sensor signal (of a sensor), and a timer. The term "timer" may refer to a clock and/or a predetermined time scheme.

The light generating system may, as can be derived from the above, in embodiments be able to operate in a single operational mode, or, in other embodiments different operational modes may be selected (e.g. via a user interface, on the bases of a sensor signal, and/or based on a timer (signal)). Herein, especially the operational mode is described wherein the light generating system provides (white) light during a first time period and then provides a boost of light, which may in general imply a lower radiant flux of light in a wavelength range below a certain wavelength but a higher radiation flux of light in a wavelength range above a certain wavelength, during a second time period. Thereafter, (during a third time period) the system may in embodiments provide light at a lower radiant flux than during the first time period (and during the second time period), or may be switched off or change to a sleeping mode. For instance, in embodiments during at least 6 hours after the second time period, no system light may be provided at all.

Hence, especially the operational mode may comprise a first time period wherein system light is provided and a second time period wherein system light is provided, wherein (i) the spectral power distribution and (ii) the radiant flux of the system light in the first time period and the second time period differ.

Therefore, in embodiments the light generating system may be configured to provide (in an operational mode) system light according to the following characteristics: (a) during a first time period $t1$ the system light is light, especially white light, having a radiant flux $\Phi11$ in a first wavelength range and a radiant flux $\Phi12$ in a second wavelength range; and (b) during a second time period $t2$ the system light is light having a radiant flux $\Phi21$ in the first wavelength range and a radiant flux $\Phi22$ in the second wavelength range. Further, especially the following characteristics may apply: $\Phi21<\Phi11$ and $\Phi22>\Phi12$. Especially, in embodiments the first time period may be at least 15 minutes, such as at least about 30 minutes. Further, in embodiments $t2$ may be selected from the range of 1 second-30 minutes, more especially at least about 30 seconds. When the radiant flux $\Phi22$ in the second wavelength range during the second time period $t2$ is high, the second time period can be shorter, whereas when the radiant $\Phi22$ in the second wavelength range during the second time period $t2$ is relatively low, the second time period may need to be longer. Especially, however, $t1>t2$.

In specific embodiments, the first wavelength range is 380 nm-$\lambda1$ and the second wavelength range is $\lambda1$-780 nm, wherein $\lambda1$ is selected from the range of 485-550 nm. Hence, in the present invention, the spectral power distribution may be divided in two parts: the wavelength range between 380 nm and $\lambda1$, and the wavelength range between $\lambda1$ and 780 nm.

After the booster light during the second time period, there may still be system light during a third time period. In general, the radiant flux thereof will be smaller than of the radiant flux during the first time period. For instance, the radiant flux (in the 380-780 nm wavelength range) during the third time period may be at least 10% lower, such as at least about 15% lower than during the first time period, or even lower, such as at least 50% lower than during the first time period. Alternatively or additionally, the system light during the third time period may have a lower CCT than of the system light during the first time period. For instance, the CCT may be lower with at least 500 K, such as at least 1000 K. As indicated also below, in some embodiments after the second time period, the system light may essentially be switched off (and there is thus no third time period). A low(er) radiant flux and/or a low(er) CCT during the third time period may reduce possible negative effects on the circadian rhythm.

Especially, $t1+t2+t3\le24$ h. For instance, $t1+t2+t3\le16$ h. Yet, in embodiments $t1+t2+t3\ge2$ h. Further, in embodiments $t1\ge t2+t3$ may apply.

Hence, in specific embodiments the light generating system may be configured to provide (in an operational mode) system light according to the following characteristics: (a) during a first time period $t1$ the system light is light, especially white light, having a radiant flux $\Phi11$ in a first wavelength range and a radiant flux $\Phi12$ in a second wavelength range; (b) during a second time period $t2$ the system light is light having a radiant flux $\Phi21$ in the first wavelength range and a radiant flux $\Phi22$ in the second wavelength range; and (c) during a third time period $t3$ the system light is light having a radiant flux $\Phi31$ in the first wavelength range and a radiant flux $\Phi32$ in the second wavelength range. Further, especially the following characteristics may also apply: $\Phi21<\Phi11$ and $\Phi31<\Phi11$. Yet further, especially the following characteristics may also apply: $\Phi22>\Phi12$, and $\Phi32<\Phi12$. Especially, as also indicated above, $t2$ may be selected from the range of 1 second-30 minutes, and especially $t1>t2$. Further, as indicated above, the first wavelength range is 380 nm-$\lambda1$ and the second wavelength range is $\lambda1$-780 nm, wherein $\lambda1$ is selected from the range of 485-550 nm.

The term "white light", and similar terms, herein, is known to the person skilled in the art. It may especially relate to light having a correlated color temperature (CCT) between about 1800 K and 20000 K, such as between 2000 and 20000 K, especially 2700-20000 K, for general lighting especially in the range of about 2000-7000 K, such as in the range of 2700 K and 6500 K. In embodiments, e.g. for backlighting purposes, or for other purposes, the correlated color temperature (CCT) may especially be in the range of about 7000 K and 20000 K. Yet further, in embodiments the correlated color temperature (CCT) is especially within about 15 SDCM (standard deviation of color matching) from the BBL (black body locus), especially within about 10 SDCM from the BBL, even more especially within about 5 SDCM from the BBL. As further elucidated below, the CCT may herein especially be selected from the range of 2000-6500 K, such as from the range of 2000-4000 K. Further note that in embodiments the CCT may vary during time, like a higher CCT during the first time period and a lower CCT during the (optional) third time period. In embodiments, the CCT of the system light may also be lower during the second time period when compared to the CCT of the system light during the first time period.

As indicated above, the system light during the first time period may be white light. In other specific embodiments, however, the system light during the first time period is visible light, but not white light. Especially, in embodiments $\Phi11/\Phi12\ge0.001$, more especially, in embodiments $\Phi11/\Phi12\ge0.005$. In embodiments, $0.001\le\Phi11/\Phi12<1$, such as $0.005\le\Phi11/\Phi12\le0.5$. Would $\Phi11$ be zero, then in general also $\Phi21$ may be zero. In general, however, herein $\Phi11/\Phi12\ge0.001$.

The terms "visible", "visible light" or "visible emission" and similar terms refer to light having one or more wavelengths in the range of about 380-780 nm. Herein, UV may especially refer to a wavelength selected from the range of 190-380 nm, such as 200-380 nm. The terms "light" and "radiation" are herein interchangeably used, unless clear from the context that the term "light" only refers to visible light. The terms "light" and "radiation" may thus refer to UV radiation, visible light, and IR radiation. In specific embodiments, especially for lighting applications, the terms "light" and "radiation" refer to (at least) visible light. The terms "violet light" or "violet emission", and similar terms, may especially relate to light having a wavelength in the range of about 380-440 nm. In specific embodiments, the violet light may have a centroid wavelength in the 380-440 nm range. The terms "blue light" or "blue emission", and similar terms, may especially relate to light having a wavelength in the range of about 440-490 nm (including some violet and cyan hues). In specific embodiments, the blue light may have a centroid wavelength in the 440-490 nm range. The terms "green light" or "green emission", and similar terms, may especially relate to light having a wavelength in the range of about 490-560 nm. In specific embodiments, the green light may have a centroid wavelength in the 490-560 nm range. The terms "yellow light" or "yellow emission", and similar terms, may especially relate to light having a wavelength in the range of about 560-590 nm. In specific embodiments, the yellow light may have a centroid wavelength in the 560-590 nm range. The terms "orange light" or "orange emission", and similar terms, may especially relate to light having a wavelength in the range of about 590-620 nm. In specific embodiments, the orange light may have a centroid wavelength in the 590-620 nm range. The terms "red light" or "red emission", and similar terms, may especially relate to light having a wavelength in the range of about 620-750 nm. In specific embodiments, the red light may have a centroid wavelength in the 620-750 nm range. The terms "cyan light" or "cyan emission", and similar terms, especially relate to light having a wavelength in the range of about 490-520 nm. In specific embodiments, the cyan light may have a centroid wavelength in the 490-520 nm range. The terms "amber light" or "amber emission", and similar terms, may especially relate to light having a wavelength in the range of about 585-605 nm, such as about 590-600 nm. In specific embodiments, the amber light may have a centroid wavelength in the 585-605 nm range.

The term "centroid wavelength", also indicated as kc, is known in the art, and refers to the wavelength value where half of the light energy is at shorter and half the light energy is at longer wavelengths; the value is stated in nanometers (nm). It is the wavelength that divides the integral of a spectral power distribution into two equal parts as expressed by the formula $\lambda c=\Sigma\lambda*I(\lambda)/(\Sigma I(\lambda))$, where the summation is over the wavelength range of interest, and $I(\lambda)$ is the spectral energy density (i.e. the integration of the product of the wavelength and the intensity over the emission band normalized to the integrated intensity). The centroid wavelength may e.g. be determined at operation conditions.

The phrase "light having one or more wavelengths in a wavelength range" and similar phrases may especially indicate that the indicated light (or radiation) has a spectral power distribution with at least intensity or intensities at these one or more wavelengths in the indicate wavelength range. For instance, a blue emitting solid state light source will have a spectral power distribution with intensities at one or more wavelengths in the 440-495 nm wavelength range.

In embodiments, it appears desirable that $R_{22,12}\ge1.05$, wherein $R_{22,12}=\Phi22/\Phi12$, to obtain the effect. Further, it may be beneficial when at the same time $R_{21,11}\le0.9$, wherein $R_{21,11}=\Phi21/\Phi11$, in order to obtain an (enhanced) effect.

Therefore, in embodiments $R_{21,11}=\Phi21/\Phi11$, and $R_{22,12}=\Phi22/\Phi12$, wherein $R_{21,11}\leq0.9$ and wherein $R_{22,12}\geq1.05$.

The radiant flux decrease below $\lambda1$ (during the second time period) may be evenly distributed over the spectral power distribution below $\lambda1$. In alternative embodiments, the radiant flux decrease below $\lambda1$ (during the second time period) may not evenly be distributed over the spectral power distribution below $\lambda1$. For instance, one or more parts of the spectral power distribution below $\lambda1$ may decrease more than one or more other parts, or even one or more parts of the spectral power distribution below $\lambda1$ may increase whereas one or more other parts decrease more (such that in total $R_{21,11}<1$).

The radiant flux increase above $\lambda1$ (during the second time period) may be evenly distributed over the spectral power distribution above $\lambda1$. In alternative embodiments, the radiant flux increase above $\lambda1$ (during the second time period) may not be evenly distributed over the spectral power distribution above $\lambda1$. For instance, one or more parts of the spectral power distribution above $\lambda1$ may increase more than one or more other parts, or even one or more parts of the spectral power distribution above $\lambda1$ may decrease whereas one or more other parts increase more (such that in total $R_{22,12}>1$). Hence, the increase of the radiant flux during the second time period in the wavelength range above $\lambda1$ and/or the decrease of the radiant flux during the second time period in the wavelength range below $\lambda1$ may be chosen such that $R_{21,11}<$, more especially $R_{21,11}\leq0.9$, and $R_{22,12}>1$, more especially $R_{22,12}\geq1.05$.

For wavelengths $\lambda1$ selected from the range of about 485-550 nm and for CCTs of system light selected from the range of about 2000-6500 K, especially selected from the range of 2000-4000 K, $R_{22,12}$ may in embodiments be up to about 5. Larger values may be possible (see also below), especially at higher CCTs and/or at higher values of the $\lambda1$ wavelength. Hence, values of the $\lambda1$ wavelength larger than 550 nm may be less desirable. Further, a CCT not higher than about 6500 K, such as not higher than 5000 K, may be desirable, as the ratio of $R_{22,12}$ may become relatively high.

In embodiments, especially at higher wavelengths of $\lambda1$, $R_{22,12}$ may get values over 5, such as even over 10. This may especially be the case when $R_{21}$, is chosen high (but still below 1). A relatively high $R_{22,12}$ may be less desirable as the sudden substantial increase in intensity may not always be liked by users. Hence, especially in embodiments $\lambda1$ and $R_{21,11}$ may be chosen such that $1.05\leq R_{22,12}\leq7$, more especially $1.05\leq R_{22,12}\leq5$. Especially, in embodiments $1.05\leq R_{22,12}\leq4$. Hence, especially $R_{22,12}\leq7$, more especially $R_{22,12}\leq5$, such as $R_{22,12}\leq4$.

In more specific embodiments, $1.05\leq R_{22,12}\leq3.0$ may apply when $\lambda1$ is selected from the range of 485-500 nm, and $2.2\leq R_{22,12}\leq5$ (such as $2.2\leq R_{22,12}\leq4$) may apply when $\lambda1$ is selected from the range of 500-550 nm. However, as indicated above, other values may also be possible, though especially at least the following may apply: $R_{21,11}<1$ and $R_{22,12}>1$, more especially $R_{21,11}\leq0.9$ and $R_{22,12}\geq1.05$ (may apply).

In specific embodiments, $R_{21,11}\leq0.8$. Yet, in specific embodiments $R_{21,11}=0$. The former embodiments, but especially the latter embodiments, may lead to colored system light during the second period. At relatively large $R_{21,11}$ values and at relatively small $R_{22,12}$ values, the system light during the second time period may be white light. However, as further elucidated below, the system light may also be colored light during the second time period.

In embodiments, the increase of the (second) radiant flux during the second time period in the wavelength range above $\lambda1$ may relatively be smaller than the decrease of the first radiant flux in the wavelength range below $\lambda1$. It may be desirable to use smaller values of $R_{22,12}$, as with a relatively small change of $R_{22,12}$, it may already be possible to have the desired effect. Hence, a substantial increase of the radiant flux above $\lambda1$ is not excluded, but may not be necessary, especially when $\lambda1$ is not chosen too high.

In specific embodiments, $R_{21,11}*R_{22,12}\leq5$. For instance, in embodiments $R_{21,11}*R_{22,12}\leq4$, such as further specific embodiments $R_{21,11}*R_{22,12}\leq2$.

At values of $\lambda1$ smaller than about 485 nm, the effect may be relatively small, and at values of $\lambda1$ larger than about 550 nm, the effect may decrease and/or may only be obtainable when using relatively substantial increases in the radiant flux ($R_{22,12}$) and/or the effect may be obtainable at lower CCTs during the first time period only. Hence, in specific embodiments, $\lambda1$ may be selected from the range of about 490-530 nm.

The higher $\lambda1$, the larger the $R_{22,12}$ may desirably be. This may lead to unpractical situations (i.e. not feasible with light sources in the room). Further, the higher the split wavelength $\lambda1$, the smaller the reduction in % active melanopsin pigment may be. From the viewpoint of efficiency the split wavelength may be chosen as low as possible, especially at least not larger than 530 nm.

In embodiments, the choice for the split wavelength $\lambda1$ can be made on the basis of a consideration related to e.g. the upper emitting wavelength of a blue primary light source. When using this split wavelength, the intensity change for wavelengths $<\lambda1$ may then be made by dimming the blue primary.

Further, in specific embodiments the system light during the first time period $t1$ may have a correlated color temperature selected from the range of 2000-6500 K, more especially selected from the range of 2000-4000 K. Hence, especially the system light during the first time period may be white light, especially with a color within 15 SDCM from the black body locus. However, in other embodiments the system light may be colored light.

Especially, the spectral power distribution of the system light during the first time period may differ from the spectral power distribution of the system light during the second time period. In specific embodiments, colors or color points of a first type of light and a second type of light may be different when the respective color points of the first type of light and the second type of light differ with at least 0.01 for u' and/or with at least 0.01 for v', even more especially at least 0.02 for u' and/or with at least 0.02 for v'. In yet more specific embodiments, the respective color points of first type of light and the second type of light may differ with at least 0.03 for u' and/or with at least 0.03 for v'. Here, u' and v' are color coordinates of the light in the CIE 1976 UCS (uniform chromaticity scale) diagram. Spectral power distributions of different sources of light having centroid wavelengths differing at least 10 nm, such as at least 20 nm, or even at least 30 nm may be considered different spectral power distributions, e.g. different colors. In general, the differences in centroid wavelengths will not be larger than about 400 nm, such as not more than 350 nm.

In embodiments, the light generating system may comprise at least two (i.e. two or more) light generating devices, configured to generate device light having different spectral power distributions. In this way, by controlling the at least two light generating devices, the spectral power distribution of the system light and the radiant flux(es) may be controlled. Therefore, in embodiments the one or more light generating devices comprise (i) a first light generating device configured to generate first device light, and (ii) a second light generating device configured to generate second device light; wherein spectral power distributions of the first device light and the second device light differ; wherein the system light comprises one or more of the first device light and the second device light.

In embodiments, one of the two or more light generating devices may be configured to generate white light having a relative low content of one or more of green, yellow, orange, and red light, whereas another one of the two or more light generating devices may be configured to generate white light having a relative high content of one or more of green, yellow, orange, and red light.

In embodiments, one of the two or more light generating devices may be configured to generate white light, whereas another one of the two or more light generating devices may be configured to generate colored light having a relative high content of one or more of green, yellow, orange, and red light.

In embodiments, one of the two or more light generating devices may be configured to generate colored light, especially having one or more wavelengths in the blue wavelength range and/or having one or more wavelengths in the green wavelength range, whereas another one of the two or more light generating devices may be configured to generate colored light having a relative high content of one or more of green, yellow, orange, and red light, while together they may provide in an operational mode white light.

In specific embodiments, the first device light may be cool white light and the second device light may be warm white light, and during the second time period t2 a contribution of the second device light to the system light may be larger than during the first time period t1. The advantage of combining cold white light and warm white light is that the light generating system, at all times, provide system light that is useful for pre-sleep human activities requiring acceptable white light conditions or sleep-preparation human activities requiring acceptable white light conditions, without impeding on the human's melatonin production in the evening and prior to sleep. Such human activities for example include winding down, reading in bed, tooth brushing before going to sleep, walking towards the bedroom, loading night-time dishwasher etc.

In (alternative) specific embodiments, the first device light may be cool white light and the second device light may be colored light having one or more wavelengths in at least one of yellow, orange, and red wavelength range, and during the second time period t2 a contribution of the second device light to the system light may be larger than during the first time period t1.

Of course, above examples may also refer to two (or more) sets of light generating devices, wherein light generating devices within a set may be configured to generate device light having essentially the same spectral power distributions, and wherein light generating devices from different sets may be configured to generate device light having different spectral power distributions. Each set may comprise at least one light generating device. The control system may be configured to control the sets individually.

In specific embodiments, the second device light may be colored light having a centroid wavelength $\lambda 2$ selected from the range of $\mu 1 < \lambda 2 \leq 780$ nm, such as selected from the range of $\lambda 1 < \lambda 2 \leq 650$ nm.

Especially, in embodiments the first device light may be white light and the second device light may be colored light having a centroid wavelength $\lambda 2$ selected from the range of $\lambda 1 < \lambda 2 \leq 650$ nm. For instance, the second device light may be green light, yellow light, orange light, or red light. Yet even more especially, the second light may be green light or yellow light. Hence, in specific embodiments the second device light may have a centroid wavelength $\lambda 2$ selected from the range of $\lambda 1 < \lambda 2 \leq 550$ nm.

When the system light is colored light during the first time period and colored light during the second time period, the centroid wavelength of the system light during the first time period may be smaller than during the second time period.

The ratio of $\Phi 31 / \Phi 11$ may be defined as $R_{31,11}$. In embodiments, wherein t3 is unequal to zero minutes, $R_{31,11} < 1$. Especially, in embodiments $R_{31,11} \leq 0.5$. The ratio of $\Phi 32 / \Phi 12$ may be defined as $R_{32,12}$. In embodiments, wherein t3 is unequal to zero minutes, $R_{32,12} < 1$. Especially, in embodiments $R_{32,12} \leq 0.5$.

In embodiments (wherein t3 is unequal to zero minutes), the spectral power distribution of the system light during the first time period and during the third time period are the same (but differ in radiant flux). In alternative embodiments (wherein t3 is unequal to zero minutes), the spectral power distribution of the system light during the second time period and during the third time period are the same (but differ in radiant flux).

Note that in alternative embodiments t3 may be 0 minutes, and thus $\Phi 31$ and $\Phi 32$ are zero (either).

In embodiments, the system may be configured to generate system light during the second time period with an illuminance, defined as the luminous flux per unit area (1 m²) incident on a surface of at least 100 lux, such as at least 250 lux, like at least 500 lux.

In embodiments (wherein t3 is unequal to zero minutes), the system may be configured to generate system light during the third time period with an illuminance, defined as the luminous flux per unit area (1 m²) incident on a surface of at maximum 100 lux, such as at maximum 50 lux, like especially at maximum 10 lux.

In embodiments an illuminance value of the system light (expressed on 'lux') during the second time period t2 is equal to or larger than, preferably larger than, an illuminance value of the system light during the first time period t1. The is, in such embodiments, the system light has a variable illuminance value $E_v$, wherein a variable illuminance value $E_v$ of the system light during the second time period t2 is equal to or larger than an illuminance value E, of the system light during the first time period t1. The same relationship of course applies for luminous flux or luminous power of the system light (expressed in 'lumen'). This is quite counterintuitive as the general teaching is to reduce light intensities prior to sleep instead of increasing light intensities.

In embodiments both a variable illuminance value E, and a variable melanopic equivalent daylight illuminance value $E_{v,mel}^{D65}$ of the system light are larger during the second time period t2 than during the first time period t1. Therefore, in embodiments the system light has a variable illuminance value $E_v$ and a variable melanopic equivalent daylight illuminance value $E_{v,mel}^{D65}$, wherein one or more of (i) the variable illuminance value $E_v$ and (ii) the variable melanopic equivalent daylight illuminance value $E_{v,mel}^{D65}$ of the system light are larger during the second time period t2 than during the first time period t1. Therefore, in embodiments the variable melanopic equivalent daylight illuminance value $E_{v,mel}^{D65}$ of the system light during the second time period t2 may be equal to or larger than during the first time period t1. Further, in embodiments both the variable illuminance value E, and the variable melanopic equivalent daylight illuminance value $E_{v,mel}^{D65}$ of the system light are smaller during the third time period t2 than during the first time period t1 and/or during the second time period t2.

The system light during the second time period t2, also referred to as the boost pulse, may be provided during relative short periods. For instance, such boost pulse may be provided shortly before going to sleep, and may e.g. last up to about 30 minutes. The time may depend upon the radiant flux. In general, the larger the radiant flux of the system light during the second period, the shorter the second period can be. Hence, the smaller the radiant flux of the system light during the second period, the longer the second period may be chosen. In embodiments, t2 may be selected from the range of at least 30 seconds, such as selected from the range of 1-15 minutes. Especially, the second time period may be no longer than 60 minutes, such as no longer than 30 minutes.

The first time period may essentially be any time period, but especially not longer than about 20 hours, such as not longer than about 16 hours. In embodiments, t1 may be at least 1 hour, such as at least about 1.5 hours. For instance, t1 may be selected from the range of 30 minutes-8 hours, such as 1-6 hours. For instance, t1 may be a period selected within the time frame of 17:00-24:00 h. Especially, the first time period may be a period during dusk.

In embodiments, the boost pulse may be provided during a period before going to sleep wherein system light is provided, whereby the boost pulse splits that period in two (or effectively three) periods, with the time preceding the boost pulse being the first period and the period succeeding the boost pulse being the third period. Optical properties like spectral power distribution and radiant flux(es) during the first time period and the third time period may be the same, but may also be different. Especially, as also indicated above, the radiant flux may be lower and/or the CCT may be lower for the system light during the third period compared to the first period. Hence, the third period may especially be a period shortly before going to sleep.

In embodiments, t3 may be at maximum 2 hours. A too long period may have a detrimental effect on the effect of the boost pulse. Hence, in embodiments t3 may be selected from the range of 0-60 minutes, such as 0-45 minutes, like in embodiments at least about 10 minutes. Especially, in embodiments t1>t3. Further, in other embodiments t3 is 0 minutes. In alternative embodiments, t3>0 minutes, such as in embodiments t3>t2. However, in yet alternative embodiments t2>t3. Especially, however, as indicated above t3≤60 minutes, more especially t3≤30 minutes, such as t3≤15 minutes, such as selected from the range of 0-15 minutes. The shorter the third time period, the higher the continued effect of the booster light pulse during the second time period may be.

As indicated above, the system may further comprise a control system configured to control the system light in dependence of one or more of an input signal of a user interface, a sensor signal (of a sensor), and a timer. In embodiments, the sensor may at least be configured to generate the sensor signal in dependence of a parameter related to behavior of a human. The sensor may be selected from a movement sensor, a presence sensor, a sound sensor, a light sensor, etc. Hence, the control system may, based on the sensor signal, learn behavior of a human using the system. For instance, routines like switching on the dishwasher, switching off specific lights, dimming light, using the stairs, using the bathroom, brushing teeth, etc., may in combination with time lead to patterns that can be recognized. In such embodiments, the system may determine a like moment a person may desire to go-to-sleep, and provide at a calculated time the boost pulse. Hence, the system may be a self-learning system in embodiments.

In embodiments, the system may comprise two or more light generating devices, wherein at least two (of the two or more light generating devices) may be configured in different rooms. This may even allow providing at spatially different positions the system light during the first period, and the system light during the second period (and the system light during the third period). Hence, in embodiments the first light generating device and the second light generating device may be configured in different spaces (in a building); wherein the first light generating device may be configured to generate during the first time period t1 the (white) system light having the radiant flux $\Phi 11$ in the first wavelength range and the radiant flux $\Phi 12$ in the second wavelength range; and wherein the second light generating device may be configured to generate during the second time period t2 the system light having the radiant flux $\Phi 21$ in the first wavelength range and the radiant flux $\Phi 22$ in the second wavelength range. In embodiments, a space wherein the first light generating device is configured may be selected from a living room and a kitchen, and wherein a space wherein the second light generating device may be configured is selected from a bathroom, a restroom, and a sleeping room.

The system may further comprise a third light generating device configured in a space different from a first space wherein the first light generating device is configured, and optionally different from a second space wherein the second light generating device is configured. In embodiment, a space wherein the third light generating device may be configured is selected from a bathroom, a restroom, and a sleeping room, especially the third light generating device may be configured in a sleeping room. In specific embodiments, three spatially different configured light generating devices, in different spaces, may be configured to generate the system light during the three mentioned time periods, respectively. In yet other specific embodiments, two spatially different configured light generating devices, in different spaces, may be configured to generate the system light during the first time period and second time period, respectively.

The light generating system may be part of or may be applied in e.g. home lighting systems, accent lighting systems, spot lighting systems, fiber-optics application systems, projection systems, self-lit display systems, pixelated display systems, segmented display systems, decorative lighting systems, etc.

In yet a further aspect, the invention also provides one or more lamps or luminaires comprising the light generating system as defined herein. The one or more luminaires may further comprise a housing, optical elements, louvres, etc., The one or more lamps or luminaires may further comprise a housing enclosing the light generating system. The one or more lamps or luminaires may comprise a light window in the housing or a housing opening, through which the system light may escape from the housing. In yet a further aspect, the invention also provides one or more projection devices comprising the light generating system as defined herein. Especially, a projection device or "projector" or "image projector" may be an optical device that projects an image (or moving images) onto a surface, such as e.g. a projection screen. The one or more projection devices may include one or more light generating systems such as described herein. Hence, in an aspect the invention also provides a light generating device selected from the group of a lamp, a luminaire, a projector device, a disinfection device, a photochemical reactor, and an optical wireless communication device, comprising the light generating system as defined
herein. The light generating device may comprise a housing
or a carrier, configured to house or support, one or more
elements of the light generating system. For instance, in
embodiments the light generating device may comprise a
housing or a carrier, configured to house or support one or
more light generating devices.

In yet a further aspect, the invention also provides a
method for generating system light (i.e. light provided by a
light generating system, especially such light generating
system as described herein), wherein the method comprises:
(a) generating during a first time period t1 system light,
especially white system light, having a radiant flux Φ11 in
a first wavelength range and a radiant flux Φ12 in a second
wavelength range; (b) generating during a second time
period t2 system light having a radiant flux Φ21 in the first
wavelength range and a radiant flux Φ22 in the second
wavelength range; and (c) optionally generating during a
third time period t3 system light having a radiant flux Φ31
in the first wavelength range and a radiant flux Φ32 in the
second wavelength range; wherein Φ21<Φ11 and
Φ31<Φ11, Φ22>Φ12, and Φ32<Φ12, t2 is selected from the
range of 1 second-30 minutes; and t1>t2; and wherein the
first wavelength range is 380 nm-λ1 and the second wave-
length range is λ1-780 nm, wherein λ1 is selected from the
range of 485-550 nm.

As indicated above, the third stage of generating during a
third time period t3 system light is optional. When available,
t3≥0 minutes (like especially at least 1 second), and when
this stage is not available, then t3=0 minutes (effectively
t3=0 seconds). Hence, the phrase "optionally during a third
time period t3" and similar phrases may refer to embodi-
ments wherein t1 and t2 are unequal zero minutes and
wherein t3 may be zero minutes or larger (but especially not
more than 2 hours, more especially not more than an hour
(see also above)). When t3=0 minutes, of course the radiant
flux Φ31 in the first wavelength range and the radiant flux
Φ32 in the second wavelength range are also zero.

BRIEF DESCRIPTION OF THE DRAWINGS

Embodiments of the invention will now be described, by
way of example only, with reference to the accompanying
schematic drawings in which corresponding reference sym-
bols indicate corresponding parts, and in which.

The schematic drawings are not necessarily to scale.

DETAILED DESCRIPTION OF THE
EMBODIMENTS

Figure 1A:
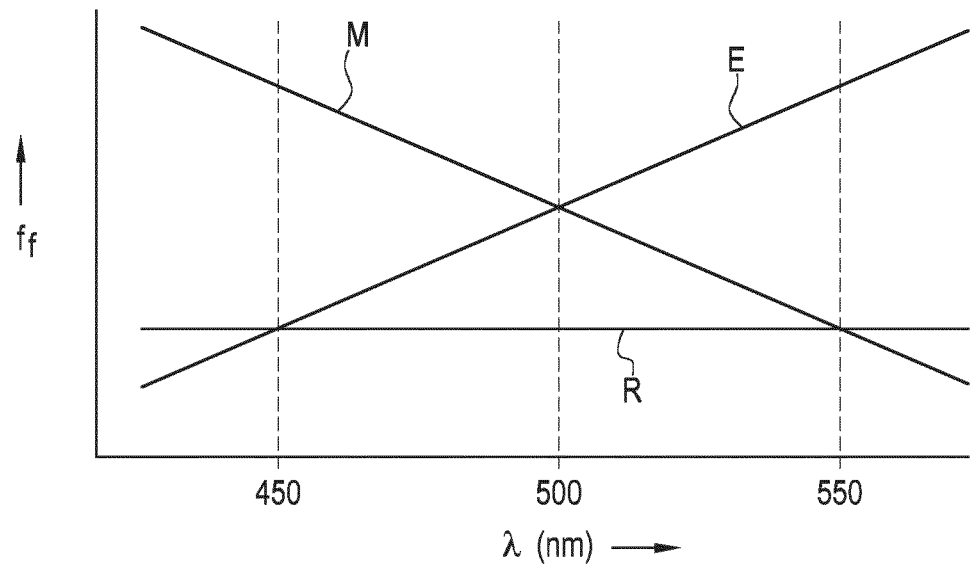
FIG. 1a schematically shows the tri-stability of melanop-
sin (see also Emanuel et al., see below). Photo-conversions
can only occur between R and M and between M and E.
Especially, the pigment fractions (at photo-equilibrium) for
stimulation by monochromatic light are depicted. On the
y-axis, schematically the fractions of the three pigment
states are schematically shown. The sum of the three frac-
tions should be equal to 1.

Current lighting applications disregard the finding
reported that the melanopsin pigment has been shown to be
tri-stable, as described by Emanuel et al. in Melanopsin
tristability for sustained and broadband phototransduction,
Neuron, 2015, 85(5), 1043-1055, doi: 10.1016/j.neu-
ron.2015.02.011, which is herein incorporated by reference.
When stimulated by light, the process of photo-conversion
(isomerization) may distribute the melanopsin pigment
across three states, two silent and one signaling. This is
schematically indicated in FIG. 1a by the labels R, M, and
E. Only the fraction of melanopsin in the signaling state (M)
can contribute to the phototransduction process in ipRGCs.
Thus, the strength of the signals sent from ipRGCs to the
SCN (signals to the brain) may be expected to depend on this
melanopsin fraction.

Whenever the spectral composition of light reaching the
melanopsin photopigment is changed, the photo-conversion
processes between states R and M, and between M and E
reach a new equilibrium. This may take time, depending on
both the spectrum and intensity of the light. The relative
spectral distribution determines the pigment fractions at the
equilibrium, the absolute intensity determines the speed of
the process. For high intensity light this may be seconds,
while low intensity light may need hours to get to this
equilibrium point. Emanuel et al. showed a number of white
light sources in their ability to change the pigment fractions.
It was found that the broad-band white light sources selected
by Emanuel et al. maintain more or less stable pigment
fractions. Further, it appears that stimulation by monochro-
matic light can change the fractions considerably.

The present invention may especially take into account
the fraction of 'signaling' melanopic pigment, thereby pro-
viding a novel and more optimized way to control the
sensitivity of the melanopic system by light, as opposed to
darkness, which seems counter-intuitive. Specifically, the
application of a short-duration and intense light to quickly
force part of the melanopsin signaling state into silence is
herein described. This approach may be counterintuitive,
since (temporary) more light (higher lux level)—not less
light—is used to reduce the melanopic activation. The
short-duration and intense light can also be extended to a
longer duration and less intense light if it is more convenient
for the end user. The duration of the shift of the tri-stable
melanopsin to a silent state will then take a longer time, but
it is still more silent than the regular whites and dimmed
situations that are normally used.

Figure 1B:
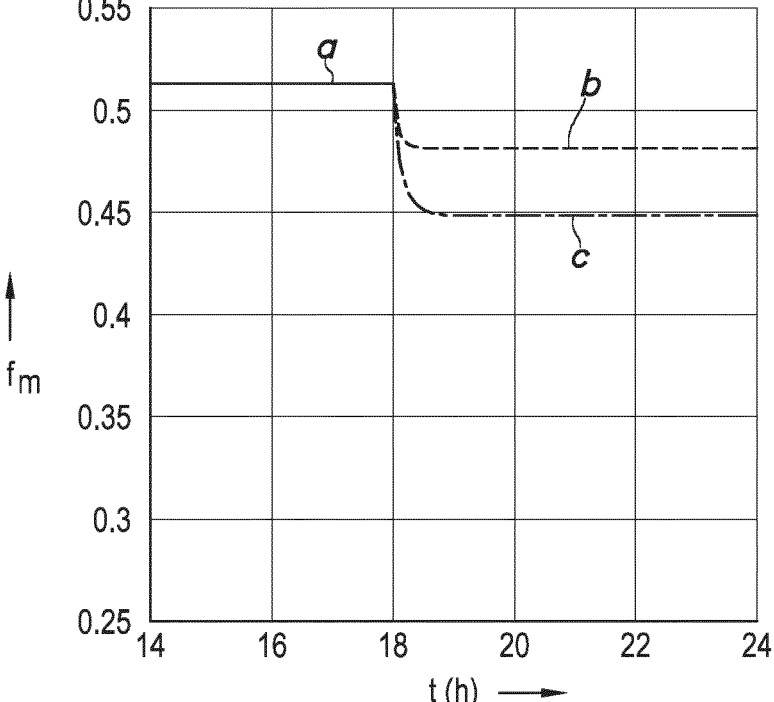
FIG. 1b shows numerical simulation of the fraction mel-
anopsin pigment in the signaling M-state. In this example, at
18 h the light spectrum changes from (a) 4000 K office light
to evening light of (b) 2700 K or (c) 2000 K.

FIG. 1b shows an example where at 18 h a change in
lighting is simulated, going from a standard office lighting
spectrum (4000K, 500 lux) to typical evening lighting at
home. For the latter, we use 2700K or 2000K at 100 lux. The
simulation shows that the pigment fraction is reduced from 0.51 to 0.48 and 0.45, respectively by changing the CCT to a lower value, and that the reduction is larger for the 2000 K light. It is expected that the lower this fraction is, the faster people may fall asleep by the reduced suppression of the melatonin production in the pineal gland.

The size of the reduction in pigment fraction, and the speed at which this occurs fully depends on the spectrum and intensity of the light. It appears that longer wavelengths may require (substantially) more time compared to the shorter wavelengths. For the present goal, however, forcing/keeping a low pigment fraction of the M-state, the shorter wavelengths should not be used (see FIG. 1a also). How much the fraction can be reduced may thus depend on the choice of the wavelengths used and the time available from the user.

Figure 1C:
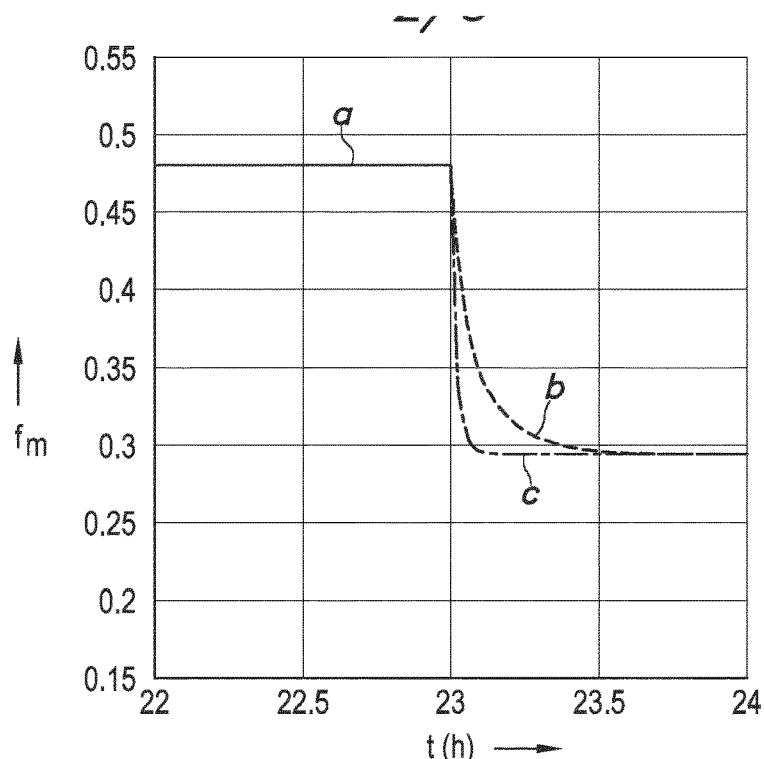
FIG. 1c shows a simulation of a change in lighting—here
at 23 h—going from 2700 K (a) to light of 525 nm, resulting
in a large reduction of the M-state pigment fraction. Note
that when 500 lux (c) is used instead of 100 lux (b), the
reduction is reached much faster.

In FIG. 1c an example is shown where a large reduction (from 0.48 to around 0.3) can be obtained using a light of wavelength 525 nm. The example also shows that when the lux level is increased from 100 lux to 500 lux, the reduction is obtained more rapidly, which is totally counter-intuitive. Roughly, a factor of 10 increase in illuminance speeds up the process by a factor of 10. The simulation shows that the pigment fraction can be considerably reduced by this invention from 0.48 to 0.3 and as such a very effective solution to prepare people to fall asleep, assuming that after the light intervention the user turns off all bedroom lighting within a reasonable short time.

Figure 2:
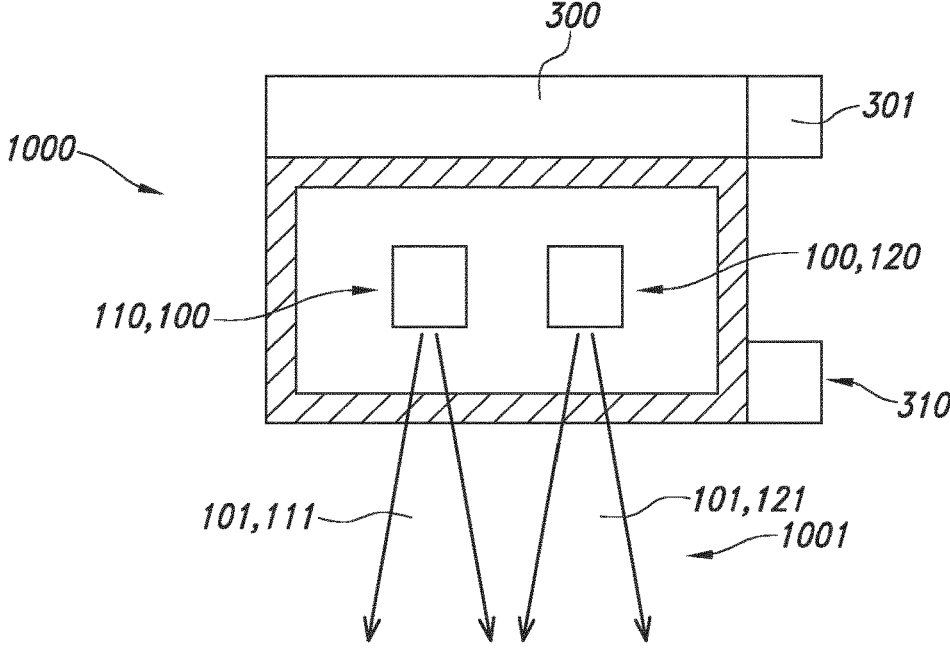
FIG. 2 schematically depicts an embodiment of the light
generating system.

Referring to FIGS. 2-3, several aspects and embodiments are (schematically) depicted.

FIG. 2 schematically depicts an embodiment of the light generating system 1000. However, many other embodiments within the scope of the claim are conceivable. The light generating system 1000 comprises one or more light generating devices 100. Each of the one or more light generating devices 100 are configured to generate device light 101. The light generating system 1000 may be configured to generate system light 1001 comprising the device light 101 of at least one light generating device 100. The light generating system 1000 may be configured to provide (in an operational mode) system light 1001 according to one or more, especially all of, the following characteristics: (a) during a first time period t1 the system light 1001 may be (white) light having a radiant flux $\Phi 11$ in a first wavelength range and a radiant flux $\Phi 12$ in a second wavelength range; (b) during a second time period t2 the system light 1001 may be light having a radiant flux $\Phi 21$ in the first wavelength range and a radiant flux $\Phi 22$ in the second wavelength range; (c) during a third time period t3 the system light 1001 may be light having a radiant flux $\Phi 31$ in the first wavelength range and a radiant flux $\Phi 32$ in the second wavelength range; (d) $\Phi 21 < \Phi 11$ and $\Phi 31 < \Phi 11$; (e) $\Phi 22 > \Phi 12$, and $\Phi 32 < \Phi 12$; (f) t2 may be selected from the range of 1 second-30 minutes; (g) t1>t2; (h) the first wavelength range may be 380 nm-$\lambda 1$ and the second wavelength range may be $\lambda 1$-780 nm; and (i) $\lambda 1$ may be selected from the range of 485-550 nm.

In embodiments, $R_{21,11}=\Phi 21/\Phi 11$, $R_{22,12}=\Phi 22/\Phi 12$, $R_{21,11}\leq 0.9$ and $R_{22,12}\geq 1.05$. In embodiments, $1.05\leq R_{22,12}\leq 5$. Especially, in embodiments $1.05\leq R_{22,12}\leq 3.0$ when $\lambda 1$ may be selected from the range of 485-500 nm and $2.2\leq R_{22,12}\leq 5$ when $\lambda 1$ may be selected from the range of 500-550 nm. In specific embodiments, $R_{21,11}*R_{22,12}\leq 5$. In embodiments, $\lambda 1$ may be selected from the range of 490-530 nm. In embodiments, the system light 1001 during the first time period t1 may have a correlated color temperature selected from the range of 2000-6500 K, more especially selected from the range of 2000-4000 K.

FIG. 2 schematically depicts an embodiment of the system 1000 wherein the one or more light generating devices 100 comprise (i) a first light generating device 110 configured to generate first device light 111, and (ii) a second light generating device 120 configured to generate second device light 121. Especially, the spectral power distributions of the first device light 111 and the second device light 121 may differ. Especially, the system light 1001 may comprise one or more of the first device light 111 and the second device light 121. Reference 301 indicates a user interface, which may optionally be comprised by the system 1000.

In specific embodiments, the first device light 111 may be cool white light and the second device light 121 may be warm white light. However, other embodiments may also be possible (see above and below).

Further, in embodiments during the second time period t2 the system light 1001 a contribution of the second device light 121 to the system light 1001 may be larger than during the first time period t1.

In embodiments, the second device light 121 may be colored light having a centroid wavelength $\lambda 2$ selected from the range of $\lambda 1 \leq \lambda 2 \leq 780$ nm.

In specific embodiments, the first device light 111 may be white light and the second device light 121 may be colored light having a centroid wavelength $\lambda 2$ selected from the range of $\lambda 1 < \lambda 2 \leq 650$ nm.

Especially, in embodiments the second device light 121 may have a centroid wavelength $\lambda 2$ selected from the range of $\lambda 1 < \lambda 2 \leq 550$ nm.

In embodiments, the system light 1001 may have a variable illuminance value $E_v$ and a variable melanopic equivalent daylight illuminance value $E_{v,mel}^{d65}$. Especially, both the variable illuminance value $E_v$ and the variable melanopic equivalent daylight illuminance value $E_{v,mel}^{d65}$ of the system light 1001 may be larger during the second time period t2 than during the first time period t1.

In embodiments, t2 may be selected from the range of 1-15 minutes. Alternatively or additionally, in embodiments t1 may be at least 1 hour. Yet alternatively or additionally, t3 may be at maximum 2 hours. In specific embodiments, t1>t3.

As also schematically depicted in FIG. 2, the light generating system 1000 may further comprise a control system 300 configured to control the system light 1001 in dependence of one or more of an input signal of a user interface, a sensor signal (of a sensor), and a timer. In embodiments, the sensor 310 may be at least configured to generate the sensor signal in dependence of the parameter related to behavior of a human.

Figure 3A:
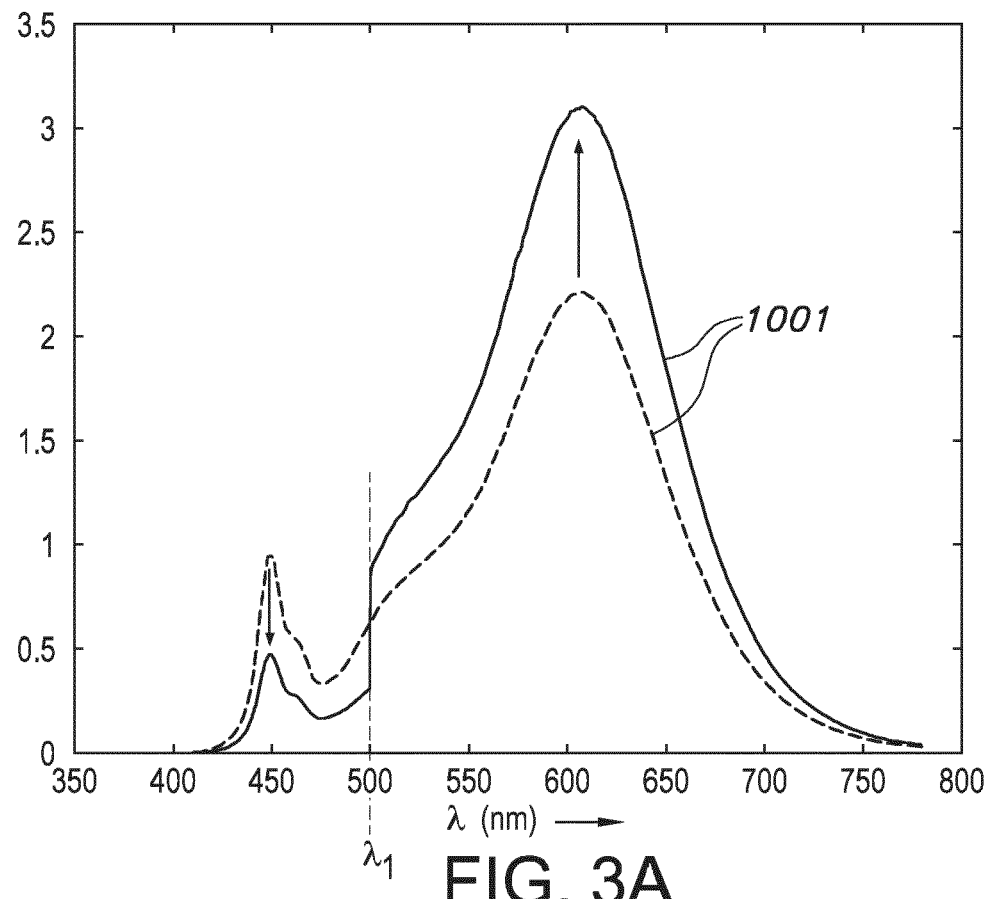
FIG. 3a schematically shows the case of a user adapted to
evening light of 2700 K, indicated by the dashed line in the
graph. 500 nm was selected as the wavelength λ1 at which the light spectrum is "splitted". To create the light boost for
improved going to sleep, the intensity of wavelengths<split
wavelength (<λ1) is reduced, while the intensity of
wavelengths>split wavelength (>λ1) is increased.

FIG. 3a schematically depicts a spectral power distribution of the system light 1001, with $\lambda 1$ at about 500 nm, and with the dashed curve the spectral power distribution during the first time period and with the filled line distribution the spectral power distribution during the second time period. Here, the intensity at all wavelengths below $\lambda 1$ is chosen to be decreased and the intensity at all wavelengths above $\lambda 1$ is chosen to be increased.

In alternative embodiments, the radiant flux decrease below $\lambda 1$ (during the second time period) may not evenly be distributed over the spectral power distribution below $\lambda 1$. For instance, one or more parts of the spectral power distribution below $\lambda 1$ may decrease more than one or more other parts, or even one or more parts of the spectral power distribution below $\lambda 1$ may increase whereas one or more other parts decrease more (such that in total $R_{21,11}<1$). Likewise, in alternative embodiments, the radiant flux increase above $\lambda 1$ (during the second time period) may not evenly be distributed over the spectral power distribution above $\lambda 1$. For instance, one or more parts of the spectral power distribution above λ1 may increase more than one or more other parts, or even one or more parts of the spectral power distribution above λ1 may decrease whereas one or more other parts increase more (such that in total $R_{22,12}>1$). As indicated above, especially $R_{21,11}=\Phi21/\Phi11$, $R_{22,12}=\Phi22/\Phi12$, $R_{21,11}\leq0.9$ and $R_{22,12}\geq1.05$.

Figure 3B:
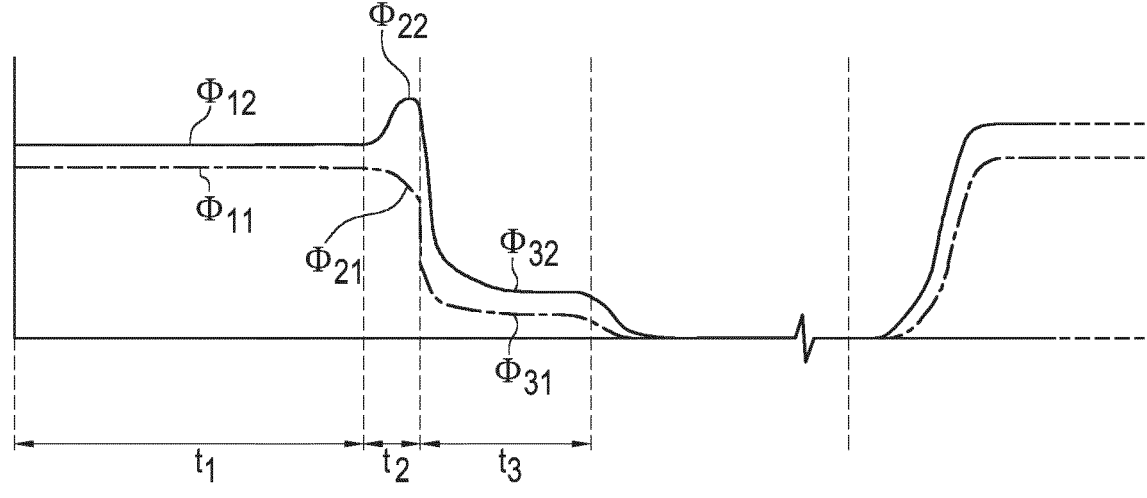
FIG. 3b schematically shows possible time dependent
radiant fluxes.

FIG. 3b shows some possible radiant fluxes over time by way of example. The booster light pulse $\Phi22$ is clearly visible in the second time period t2.

For different intensity reduction factors (for wavelengths<split wavelength), the minimally required multiplication factors for wavelengths>split to create the light boost were determined.

Figure 3C:
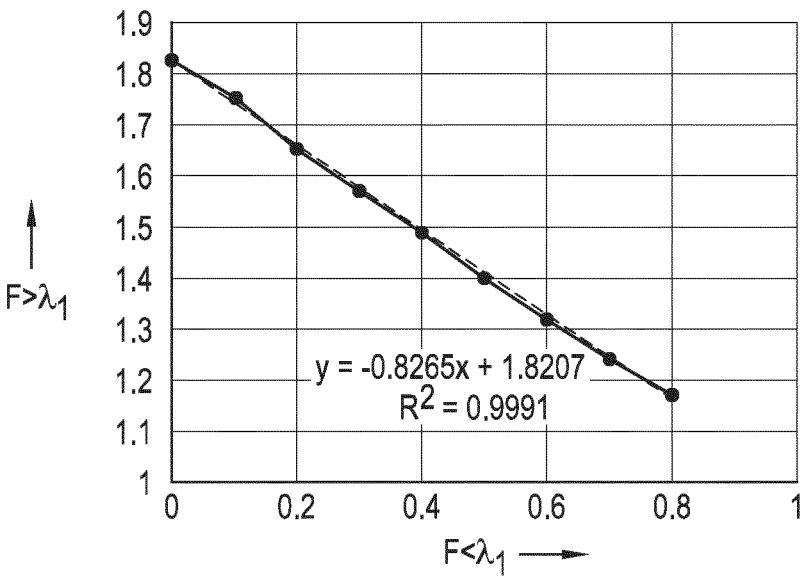
FIG. 3c shows an example for a multiplication factor, here
for embodiments with the system light having a CCT of
2700 K in the first time period, and λ1=500 nm.

The tables below and FIG. 3c show an exemplary curve for λ1=500 nm for the 2700 K. In below tables, some further results for the multiplication factors are provided. Herein, λ1 indicates the wavelength where the spectral power distribution is divided in a part below (<λ1) and in part above (>λ1). The values are provided at different CCT. The multiplication factors are determined for a booster light pulse time of 5 minutes.

| 2000 K | | |
|---|---|---|
| split wavelength <λ1 (nm) | multiplication factor <λ1 R21, 11 | multiplication factor minimum <λ1 R22, 12 | multiplication factor maximum <λ1 R22, 12 |
| 485 | 0 | 1.34 | 5.36 |
| | 0.4 | 1.205 | 4.82 |
| | 0.8 | 1.068 | 4.27 |
| 500 | 0 | 1.585 | 6.34 |
| | 0.4 | 1.35 | 5.4 |
| | 0.8 | 1.115 | 4.46 |
| 530 | 0 | 3.43 | 13.7 |
| | 0.4 | 2.45 | 9.8 |
| | 0.8 | 1.48 | 5.92 |
| 550 | 0 | 8.1 | 32.4 |
| | 0.4 | 5.25 | 21.0 |
| | 0.8 | 2.45 | 9.8 |

| 2700 K | | |
|---|---|---|
| split wavelength λ1 (nm) | multiplication factor <λ1 R21, 11 | multiplication factor minimum <λ1 R22, 12 | multiplication factor maximum <λ1 R22, 12 |
| 520 | 0.05 | 3 | 12 |
| | 0.1 | 2.9 | 11.6 |
| | 0.2 | 2.7 | 10.8 |
| | 0.3 | 2.5 | 10 |
| | 0.5 | 2.1 | 8.4 |
| | 0.8 | 1.42 | 5.68 |
| 510 | 0.05 | 2.25 | 9 |
| | 0.1 | 2.15 | 8.6 |
| | 0.2 | 2.05 | 8.2 |
| | 0.3 | 1.9 | 7.6 |
| | 0.5 | 1.65 | 6.6 |
| | 0.8 | 1.25 | 5 |
| 500 | 0 | 1.82 | 7.28 |
| | 0.1 | 1.75 | 7 |
| | 0.2 | 1.65 | 6.6 |
| | 0.3 | 1.57 | 6.28 |
| | 0.4 | 1.49 | 5.96 |
| | 0.5 | 1.4 | 5.6 |
| | 0.6 | 1.32 | 5.28 |
| | 0.7 | 1.24 | 4.96 |
| | 0.8 | 1.17 | 4.68 |

-continued

| 2700 K | | |
|---|---|---|
| split wavelength λ1 (nm) | multiplication factor <λ1 R21, 11 | multiplication factor minimum <λ1 R22, 12 | multiplication factor maximum <λ1 R22, 12 |
| 485 | 0 | 1.46 | 5.84 |
| | 0.3 | 1.325 | 5.3 |
| | 0.5 | 1.23 | 4.92 |
| | 0.8 | 1.095 | 4.38 |
| 550 | 0 | 11.65 | 46.6 |
| | 0.5 | 6.35 | 25.4 |
| | 0.8 | 3.15 | 12.6 |
| 530 | 0 | 4.5 | 18 |
| | 0.3 | 3.46 | 13.84 |
| | 0.5 | 2.76 | 11.04 |
| | 0.8 | 1.71 | 6.84 |

| 4000 K | | |
|---|---|---|
| split wavelength λ1 (nm) | multiplication factor <λ1 R21, 11 | multiplication factor minimum <λ1 R22, 12 | multiplication factor maximum <λ1 R22, 12 |
| 485 | 0 | 1.8 | 7.2 |
| | 0.4 | 1.475 | 5.9 |
| | 0.8 | 1.16 | 4.6 |
| 500 | 0 | 2.2 | 8.8 |
| | 0.4 | 1.72 | 6.9 |
| | 0.8 | 1.24 | 5.0 |
| 530 | 0 | 5.3 | 21.2 |
| | 0.4 | 3.56 | 14.2 |
| | 0.8 | 1.86 | 7.4 |
| 550 | 0 | 15.6 | 62.4 |
| | 0.4 | 9.8 | 39.2 |
| | 0.8 | 3.95 | 15.8 |

The tables above are directed to embodiments wherein the system light during the first time period is white light. For colored light during the first time period, the same multiplication factors may be applied.

From the tables above, it appears that at higher CCTs and with larger split wavelengths, even the minimum multiplication factor or ratio R22,12 can become larger than 5 (see e.g. the split wavelength of 550 nm with a minimum ratio R22,12 of 15,6 for one entry. Should one desire to stay below a value of 5, then the multiplication factor of the lower wavelength range (<λ1) may be adapted and/or the split wavelength may be adapted (i.e. in this example of 550 nm: lowered below 550 nm). Note that, as indicated above, 550 nm is anyhow a relatively large wavelength. Especially, λ1 may be selected from the range of 490-530 nm.

Figure 4A:
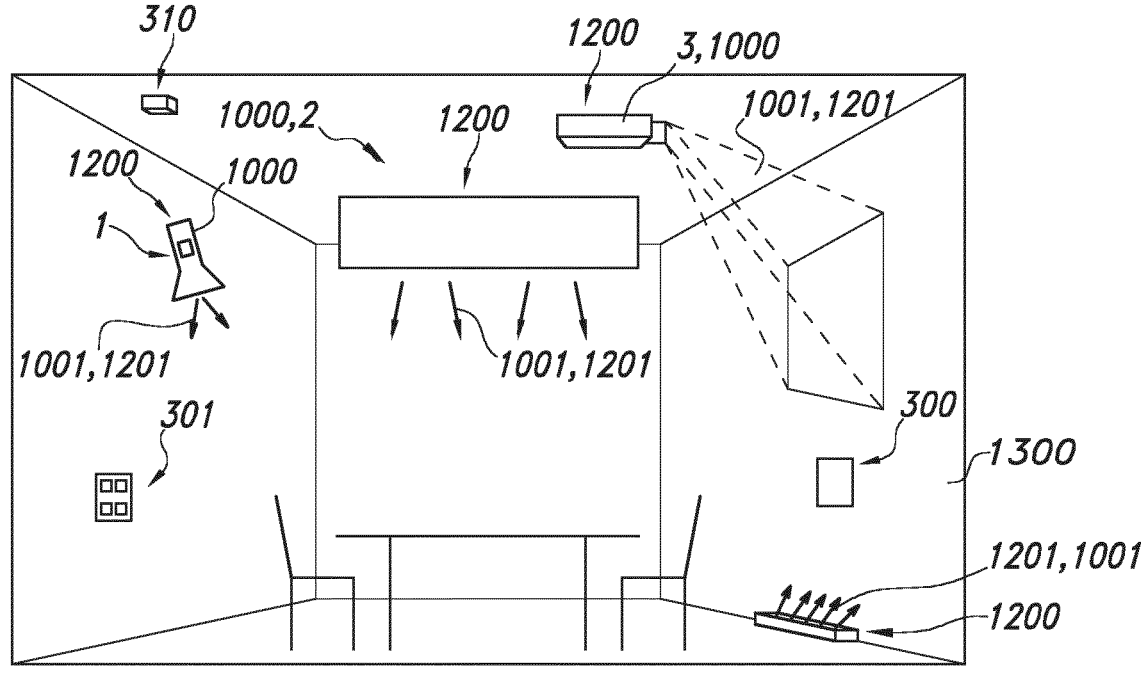
FIGS. 4a-4b schematically depict some further (applica-
tion) embodiments.

FIG. 4a schematically depicts an embodiment of a luminaire 2 comprising the light generating system 1000 as described above. Reference 301 indicates a user interface which may be functionally coupled with the control system 300 comprised by or functionally coupled to the light generating system 1000. FIG. 4a also schematically depicts an embodiment of lamp 1 comprising the light generating system 1000. Reference 3 indicates a projector device or projector system, which may be used to project images, such as at a wall, which may also comprise the light generating system 1000. Hence, FIG. 4a schematically depicts embodiments of a lighting device 1200 selected from the group of a lamp 1, a luminaire 2, a projector device 3, a disinfection device, a photochemical reactor, and an optical wireless communication device, comprising the light generating system 1000 as described herein. In embodiments, such lighting device may be a lamp 1, a luminaire 2, a projector device 3, a disinfection device, or an optical wireless communication device. Lighting device light escaping from the lighting device 1200 is indicated with reference 1201. Lighting device light 1201 may essentially consist of system light 1001, and may in specific embodiments thus be system light 1001.

Figure 4B:
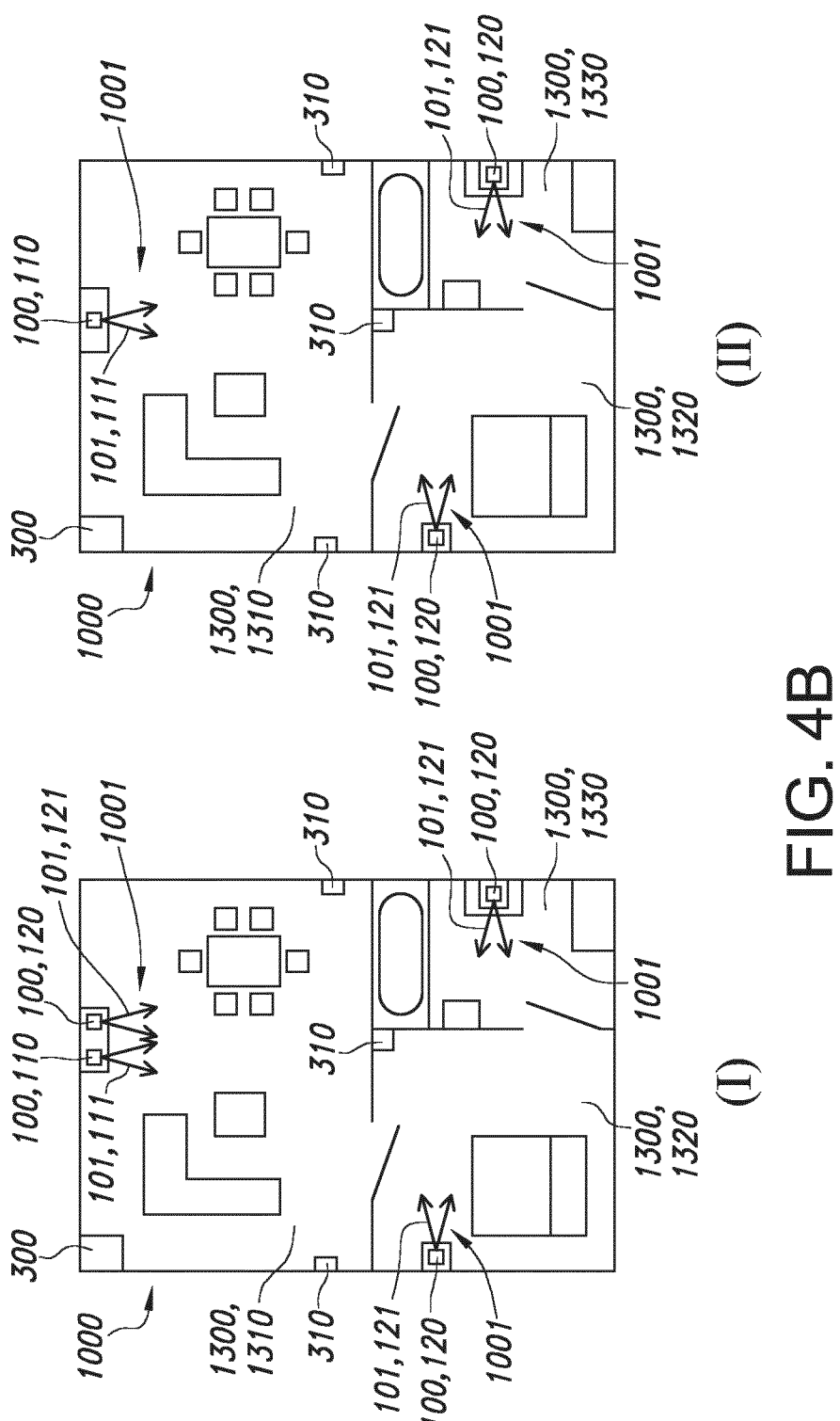

Referring to FIG. 4*b*, the light generating system 1000 may comprise a first light generating device 110 and a second light generating device 120, which may be configured in different spaces. The first light generating device 110 may be configured to generate during the first time period t1 the white system light 1001 having the radiant flux Φ11 in the first wavelength range and the radiant flux Φ12 in the second wavelength range. The second light generating device 120 may be configured to generate during the second time period t2 the system light 1001 having the radiant flux Φ21 in the first wavelength range and the radiant flux Φ22 in the second wavelength range. The first light generating device 110 may be configured in a space selected from a living room and a kitchen. The second light generating device 120 may be configured in a space selected from a bathroom, a restroom, and a sleeping room. The different spaces 1300 are indicated with references 1310, 1320, and 1330, respectively. Of course more than two different spaces may be illuminated with the device light of one or more of the light generating devices. In embodiment I of FIG. 4*b*, the first light generating device 110 is configured in a living room 1310. Further, the second light generating device 120 is also configured in the living room 1310, but second light generating devices may also be configured in the sleeping room 1320 and/or the restroom 1330. This may allow a booster pulse in the living room, and optionally system light 1001 at reduced intensity and/or reduced CCT in the sleeping room 1320 and/or the restroom 1330 during the third period. However, it may also allow a booster pulse in the sleeping room 1320 and/or the restroom 1330, and optionally system light 1001 at reduced intensity and/or reduced CCT in the sleeping room 1320 and/or the restroom 1330 during the third period. Whereas in embodiment I the system light 1001 in the living room 1310 may be provided by contributions of both the first device 110 and the second device 120, in embodiment II of FIG. 4*b*, the system light 1001 may be provided in the living room 1310 by device light 111 only. In such embodiments, e.g. a booster pulse in the sleeping room 1320 and/or the restroom 1330 may be provided, and optionally system light 1001 may be provided at reduced intensity and/or reduced CCT in the sleeping room 1320 and/or the restroom 1330 during the third period Amongst others, the invention provides a lighting system with at least one light setting providing for a "high intensity" setting with a dominant wavelength of e.g. 485 nm or higher to be applied prior to going asleep. The duration of the go-to-sleep routine can be set at user's preference (optional) as to tune the intensity and even the color tone upon preference. Calculations show that the duration and the illuminance are exchangeable. So, 1 minute of 500 lux has the same effect as 5 minutes of 100 lux. Further, longer wavelengths may require more time to reach the same effect as a shorter wavelength. The boost light does not have to be a single wavelength, it can be broadband with the restriction that wavelengths<485 nm are substantially not to be used. For example, switching off the blue LED in a white light spectrum from a Hue lamp, resulting in yellowish light, already is a first approximation to such a broadband light spectrum.

In embodiments, the invention provides a lighting system with a control unit, receiving control signals based on knowledge of the go-to-bed routine of the user (e.g. HUE go-to-sleep routine). The control signals can either be calculated on the fly or can be precalculated to evoke a light effect as described below.

In embodiments, the invention provides a connected lighting system, either receiving input from a (co-located) sensor or sensors, capable of assessing or inferring the current 'state' of the user, where state refers to the user's lighting history, or deriving this current state based on a model, e.g. from prior history.

In embodiments, the invention provides a bulb that when the (wall) switch is turned off automatically provides first for the light boost before dimming to complete darkness.

In embodiments, the invention provides a connected bathroom lighting system that switches on the boost light when it detects or receives a control signal that a user starts using an electric toothbrush in the evening (prior to going to sleep).

The term "plurality" refers to two or more.

The terms "substantially" or "essentially" herein, and similar terms, will be understood by the person skilled in the art. The terms "substantially" or "essentially" may also include embodiments with "entirely", "completely", "all", etc. Hence, in embodiments the adjective substantially or essentially may also be removed. Where applicable, the term "substantially" or the term "essentially" may also relate to 90% or higher, such as 95% or higher, especially 99% or higher, even more especially 99.5% or higher, including 100%.

The term "comprise" also includes embodiments wherein the term "comprises" means "consists of".

The term "and/of" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices, apparatus, or systems may herein amongst others be described during operation. As will be clear to the person skilled in the art, the invention is not limited to methods of operation, or devices, apparatus, or systems in operation.

It should be noted that the above-mentioned embodiments illustrate rather than limit the invention, and that those skilled in the art will be able to design many alternative embodiments without departing from the scope of the appended claims.

In the claims, any reference signs placed between parentheses shall not be construed as limiting the claim.

Use of the verb "to comprise" and its conjugations does not exclude the presence of elements or steps other than those stated in a claim. Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

The article "a" or "an" preceding an element does not exclude the presence of a plurality of such elements.

The invention may be implemented by means of hardware comprising several distinct elements, and by means of a suitably programmed computer. In a device claim, or an apparatus claim, or a system claim, enumerating several means, several of these means may be embodied by one and the same item of hardware. The mere fact that certain measures are recited in mutually different dependent claims does not indicate that a combination of these measures cannot be used to advantage. In yet a further aspect, the invention (thus) provides a software product, which, when running on a computer is capable of bringing about (one or more embodiments of) the method as described herein.

The invention also provides a control system that may control the device, apparatus, or system, or that may execute the herein described method or process. Yet further, the invention also provides a computer program product, when running on a computer which is functionally coupled to or comprised by the device, apparatus, or system, controls one or more controllable elements of such device, apparatus, or system.

The invention further applies to a device, apparatus, or system comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Further, the person skilled in the art will understand that embodiments can be combined, and that also more than two embodiments can be combined. Furthermore, some of the features can form the basis for one or more divisional applications.

The invention claimed is:

1. A light generating system comprising one or more light generating devices, wherein each of the one or more light generating devices are configured to generate device light, wherein the light generating system is configured to generate system light comprising the device light of at least one light generating device, wherein the light generating system is configured to provide system light according to the following characteristics:

during a first time period t1 the system light is white light having a radiant flux $\Phi 11$ in a first wavelength range and a radiant flux $\Phi 12$ in a second wavelength range;

during a second time period t2 the system light is light having a radiant flux $\Phi 21$ in the first wavelength range and a radiant flux $\Phi 22$ in the second wavelength range;

during a third time period t3 the system light is light having a radiant flux $\Phi 31$ in the first wavelength range and a radiant flux $\Phi 32$ in the second wavelength range;

$\Phi 21 < \Phi 11$ and $\Phi 31 < \Phi 11$ $\Phi 22 > \Phi 12$, and $\Phi 32 < \Phi 12$ t2 is selected from the range of 1 second-30 minutes; and t1>t2;

the first wavelength range is 380 nm-$\lambda 1$ and the second wavelength range is $\lambda 1$-780 nm, wherein $\lambda 1$ is selected from the range of 485-550 nm, wherein the one or more light generating devices comprise (i) a first light generating device configured to generate cool white light, and (ii) a second light generating device configured to generate warm white light; wherein spectral power distributions of the first device light and the second device light differ; wherein the system light comprises one or more of the cool white light and the warm white light; and wherein during the second time period t2 a contribution of the warm white light to the system light is larger than during the first time period t1.

2. The light generating system according to claim 1, wherein the system light has a variable luminous flux or illuminance value $E_v$, wherein the variable luminous flux or illuminance value $E_v$ of the system light during the second time period t2 is equal to or larger than during the first time period t1.

3. The light generating system according to claim 1, wherein $1.05 \leq R_{22,12} \leq 5$, wherein $R_{22,12} = \Phi 22 / \Phi 12$.

4. The light generating system according to claim 1, wherein $1.05 \leq R_{22,12} \leq 3.0$ when $\lambda 1$ is selected from the range of 485-500 nm and wherein $2.2 \leq R_{22,12} \leq 5$ wherein $\lambda 1$ is selected from the range of 500-550 nm, wherein $R_{22,12} = \Phi 22 / \Phi 12$.

5. The light generating system according to claim 1, wherein $R_{21,11} * R_{22,12} \leq 5$, wherein $R_{21,11} = \Phi 21 / \Phi 11$ and $R_{22,12} = \Phi 22 / \Phi 12$.

6. The light generating system according to claim 1, wherein the system light during the first time period t1 has a correlated color temperature selected from the range of 2000-6500 K and a color point within 15 standard deviation of color matching from the black body locus.

7. The light generating system according to claim 1, wherein the system light has a variable melanopic equivalent daylight illuminance value $E_{v,mel}^{D65}$, wherein the variable melanopic equivalent daylight illuminance value $E_{v,mel}^{D65}$ of the system light during the second time period t2 is equal to or larger than during the first time period t1.

8. The light generating system according to claim 1, wherein t2 is selected from the range of 1-15 minutes; wherein t1 is at least 1 hour, and wherein t3 is selected from the range of 0-60 minutes; and wherein t1>t3.

9. The light generating system according to claim 1, further comprising a control system configured to control the system light in dependence of one or more of an input signal of a user interface, a sensor signal, and a timer.

10. The light generating system according to claim 9, wherein a sensor is at least configured to generate the sensor signal in dependence of the parameter related to behavior of a human.

11. The light generating system according to claim 1, wherein the first light generating device and the second light generating device are configured in different spaces; wherein the first light generating device is configured to generate during the first time period t1 the cool white light having the radiant flux $\Phi 11$ in the first wavelength range and the radiant flux $\Phi 12$ in the second wavelength range; and wherein the second light generating device is configured to generate during the second time period t2 the warm white light having the radiant flux $\Phi 21$ in the first wavelength range and the radiant flux $\Phi 22$ in the second wavelength range.

12. The light generating system according to claim 1, wherein the first light generating device and/or the second light generating device are comprised in a lighting device selected from the group of a lamp, a luminaire, a projector device and an optical communication device.

* * * * *